United States Patent [19]

Lloyd

[11] Patent Number: 5,119,023
[45] Date of Patent: Jun. 2, 1992

[54] METHOD AND APPARATUS FOR EDDY CURENT NON-DESTRUCTIVE EXAMINATION OF CYLINDRICAL METALLIC MEMBERS

[75] Inventor: Edward A. Lloyd, Culcheth, United Kingdom

[73] Assignee: NNC Limited, England

[21] Appl. No.: 481,207

[22] Filed: Feb. 20, 1990

[51] Int. Cl.⁵ .................... G01N 27/72; G01R 33/12
[52] U.S. Cl. .................................. 324/239; 324/220; 324/242; 324/243
[58] Field of Search ................. 324/219–221, 324/239–243, 225

[56] References Cited

U.S. PATENT DOCUMENTS

| | | | |
|---|---|---|---|
| 2,555,853 | 6/1951 | Irwin | 324/242 |
| 3,875,502 | 4/1975 | Neumaier | 324/37 |
| 4,742,298 | 5/1988 | Ando et al. | 324/220 |

FOREIGN PATENT DOCUMENTS

| | | |
|---|---|---|
| 0019091 | 11/1980 | European Pat. Off. |
| 2326391 | 12/1974 | Fed. Rep. of Germany |
| 58-34357 | 2/1983 | Japan |
| 1303783 | 1/1973 | United Kingdom |
| 1315468 | 5/1973 | United Kingdom |

Primary Examiner—Walter E. Snow
Attorney, Agent, or Firm—Kirschstein, Ottinger, Israel & Schiffmiller

[57] ABSTRACT

A method and apparatus for non-destructively examining cylindrical material by electromagnetic induction use primary coils separated by an annular gap. The primary coils are excited oppositely so that the respective magnetic fields thereby generated are in boosting relationship in the gap. Close electromagnetic coupling of the primary coils with the material under examination is effected, and detectors, such as secondary coils are disposed in the gap to detect flux perturbations caused by variation in the properties of the material under examination.

6 Claims, 2 Drawing Sheets

METHOD AND APPARATUS FOR EDDY CURENT NON-DESTRUCTIVE EXAMINATION OF CYLINDRICAL METALLIC MEMBERS

BACKGROUND OF THE INVENTION

1. Field of the Invention

This invention relates to a method of non-destructive examination by electromagnetic induction of metallic material in cylindrical solid or tubular form. It relates also to apparatus for this purpose.

2. Description of Related Art

By electromagnetic induction, eddy currents are generated in the metallic material under examination as a result of AC excitation of a primary coil or coils, and the perturbation of the eddy currents caused by variations in the properties of the material gives rise to modifications of the associated magnetic field which are detectable by a secondary coil or coils, or by other suitable detector means.

For the examination of metallic material in cylindrical form, most commonly tubular cylindrical material such as pipe or tube, a close electromagnetic coupling of the primary coil with the material, as distinct from a remote field arrangement, is effected by sizing the coil to fit closely, even contiguously, around the outer diameter of the material, or around the inner diameter if the form is tubular. Such coupling is effective over the full circumference of the material and is an aid against the phenomenon of so-called "lift-off" which is a variability of the coupling giving rise to interfering signals in the conduct of the examination. However, with close electromagnetic coupling there is precluded the arrangement, of which examples are already known, in which a secondary coil or coils for detection purposes is or are interposed between the primary coil or coils and the material under examination.

SUMMARY OF THE INVENTION

According to one aspect of the invention there is provided a method of non-destructive examining by electromagnetic induction a metallic material in cylindrical solid or tubular form, comprising closely electromagnetically coupling with the material primary coils which are separated by an annular gap, the primary coils being closely fitted around the outer diameter, or the inner diameter if present, of the material; oppositely exciting the primary coils by alternating current such that the respective magnetic fluxes thereby produced are in boosting relationship in the gap; detecting in the gap at a discrete location circumferentially thereof flux perturbations caused by variations in the properties of the material in the vicinity of that location; and shifting in a circumferential sense the location at which the detection as aforesaid is operative in order that the position in the material of any detected variation in the properties thereof is ascertainable from the location at which the detection is operative at the time and the position of the primary coils along the length of the material.

According to another aspect of the invention there is provided non-destructive examination apparatus operable by electromagnetic induction for examining metallic material in cylindrical solid or tubular form, comprising primary coils separated by an annular gap and sized for close electromagnetic coupling with the material by fitting around the outer diameter thereof, or the inner diameter if present; a high-frequency alternating current generator for exciting the primary coils oppositely such that the respective magnetic fluxes thereby produced are in boosting relationship in the gap; detector means disposed in the gap to detect flux perturbations caused by variations in the properties of the material in the vicinity of the detector means; and means to shift circumferentially the location at which the detector means is operative in order that the position in the material of any detected variation in the properties thereof is ascertainable from the location at which the detection means is operative at the time and the position of the primary coils along the length of the material.

Detection in the gap of the flux perturbations may be by means of magneto-diodes, Hall effect devices or secondary coils. In the case of secondary coils, the coil axis is preferably arranged radial to the axis of the primary coils, an arrangement which aids narrowing the width of the gap to a minimum thereby to achieve utmost concentration of the magnetic flux generated in the gap.

With a ring of detectors, such as secondary coils each orientated radially of the axis of the primary coils, a sequential sampling of each detector in turn enables by displacement of the combination lengthwise of the material the execution of a helical scan. This is a technique to be preferred over the alternative of physically rotating the combination simultaneously with the lengthwise displacement which is apt to create difficulties with mechanical stability and durability. For robustness, especially where use is to be inside pipe or tube in the style of a pig for passing along the bore, the combination is preferably in a fully encapsulated assembly containing also such commutation as may be needed for the sampling of multiple detectors, suitably in solid state form.

BRIEF DESCRIPTION OF THE DRAWINGS

An embodiment of the invention will now be described, by way of example, with reference to the accompanying drawing in which.

DETAILED DESCRIPTION OF THE PREFERRED EMBODIMENT

Figure 1:
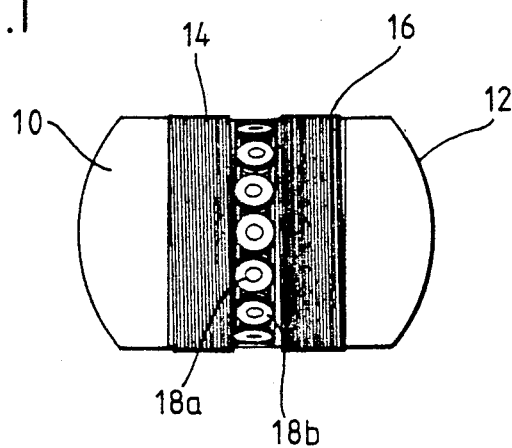
FIG. 1 is a diagrammatic elevation of a pig component for use in the examination of boiler tubes.

The pig of FIG. 1 is for travelling along the interior of a boiler tube to be examined, such tube being, for example, in or for the steam generator of a pressurised water nuclear reactor and therefore being of a suitable type of alloy steel. The diameter of the pig is uniform over its whole length and is sized, inclusive of encapsulation, to be an easy sliding fit within the bore of the tube.

Between two end pieces 10 and 12 are pimary coils 14 and 16 which are wound co-axially to the full diameter for maximising the closeness of the electromagnetic coupling around the full circumference of the tube wall. In an annular gap defined between adjacent ends of the primary coils are disposed a ring of secondary coils, such as those referenced 18a and 18b, which have their axes radial to the pig axis, so as to detect the radial component of the primary flux. Such secondary coils are spaced equiangularly and are closely packed in the ring to maximise their number, there being sixteen in the present example. They may conveniently be wound on cores projecting radially from a common cylindrical former (not visible in the drawings).

Figure 2:
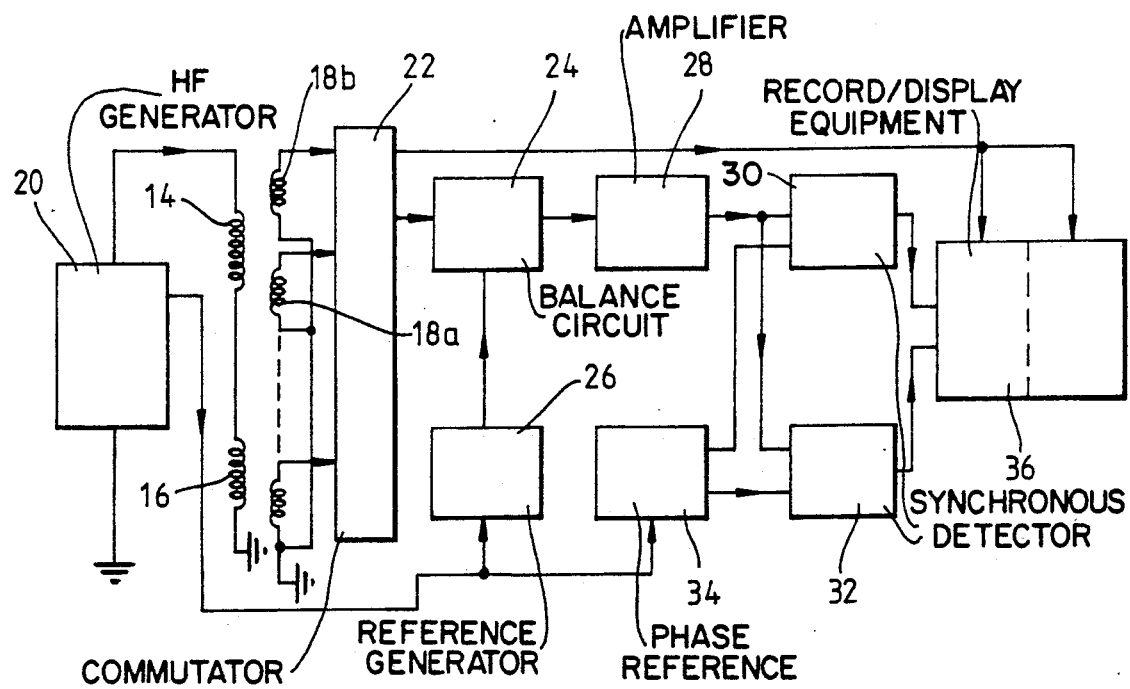
FIG. 2 is a block diagram of the main components of signal processing circuitry.
Figure 3:
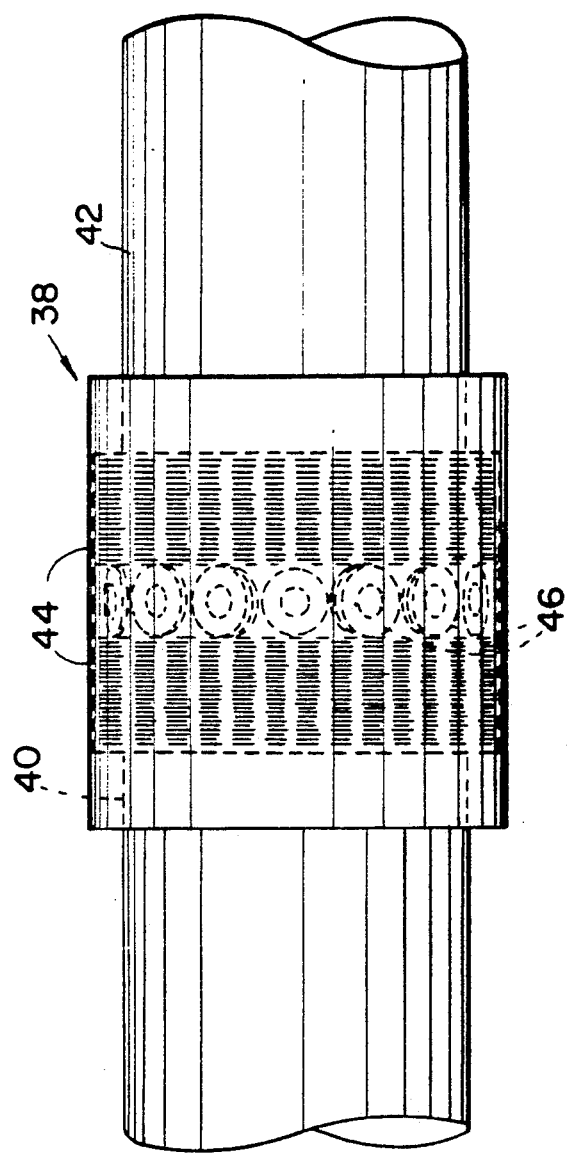
FIG. 3 is a schematic pictorial view of a component, similar to FIG. 1, for examining a solid metallic member.

Referring to FIG. 2, a high frequency electric current generator 20, preferably having multi-frequency selection, is arranged to drive current through the primary coils 14 and 16, which are wound oppositely on the pig so as to be oppositely excited, thereby to produce in the gap occupied by the secondary coils a boosting relationship of the magnetic fluxes set up by the primary coils. The secondary coils 18a, 18b etc are connected individually to a commutator 22, preferably based on solid state switching and therefore miniaturised for inclusion in the pig itself. The function of the commutator is to sample sequentially the signals from the secondary coils in continuously repeated cycles, the signals so sampled being fed serially to a balance circuit 24 which effects balancing with reference to a signal derived from the generator 20 through an appropriately adjusted reference signal generator 26.

Signals indicative of property variations in the tube wall which arise from imbalance in the circuit 24 are amplified in an amplifier 28 and are fed to synchronous detectors 30 and 32 which derive phase reference signals from the generator 20 through phase reference circuitry 34. From the synchronous detectors the output may be displayed and/or recorded, as desired, by use of appropriate equipment 36.

In the illustrated example the primary coils 14 and 16 are balanced, that is to say, each having like flux generating capacity. This is a convenience but is not essential since an imbalance can be compensated in the balance circuit 24. The normal eddy current distribution to which the flux gives rise in the tube wall undergoes perturbation in response to property variations encompassing such phenomena as cracking by stress corrosion or fatigue, dimensional variations, non-uniformity of composition, and localised degradation, such as intergranular attack. The modifications which these perturbations cause in the magnetic field concentrated in the annular gap between the primary coils are sensed by the secondary coils, the field being concentrated for increasing sensitivity by narrowing to the utmost the width of the annular gap and, for this purpose, limiting the lateral dimensions of the detector means (the secondary coils in this example) to as little as is compatible with optimum operation.

Travel of the pig down the tube will be in a fixed angular orientation. Rotation is unnecessary since the sequential sampling of the detector means achieves a pseudo-rotative effect. The switching rate for the sequential sampling will of course be correlated with the rate of travel down the tube according to closeness of scan desired. Also the choice of different exitation frequencies for the primary coils enables, in known manner, a variation in the range to which examination is extended depthwise in the tube wall and beyond. Hence, with co-ordinates available for both angular and lengthwise positions, it is possible with the appropriate record/display equipment to reproduce the examination data in the form of an isometric map.

For use externally of cylindrical material to be examined, as is necessary with material of solid section;

I claim:

1. A method of non-destructively examining by electromagnetic induction a metallic material in cylindrical solid or tubular form, comprising: closely electromagnetically coupling with said material primary coils which are separated by an annular gap, said primary coils being closely fitted around the outer diameter, or the inner diameter if present, of said material; oppositely exciting said primary coils by alternating current such that the respective primary magnetic fluxes thereby produced are in boosting relationship in said gap; detecting in said gap at a discrete location circumferentially thereof perturbations in a radial component of said primary magnetic flux caused by variations in properties of said material in the vicinity of that location; and shifting in a circumferential sense the location at which the detection as aforesaid is operative in order that the position in the material of any detected variation in the properties thereof is ascertainable from the location at which the detection is operative at the time and the position of the primary coils along the length of said material.

2. A method as claimed in claim 1, in which said shifting of the location at which the detection is operative is accomplished by sampling in sequence a ring of detectors disposed in the annular gap between the primary coils.

3. A method as claimed in claim 1, in which said shifting of the location at which the detection is operative is carried out simultaneously with displacement of said primary coils lengthwise of said material so as to execute a helical scan for variations in the properties therof.

4. Non-destructive examination apparatus operable by electromagnetic induction for examining metallic material in cylindrical solid or tubular form, comprising: primary coils separated by an annular gap and sized for close electromagnetic coupling with said material by fitting around the outer diameter thereof, or the inner diameter if present; a high-frequency alternating current generator for exciting said primary coils oppositely such that the respective primary magnetic fluxes thereby produced are in boosting relationship in said gap; detector means disposed in said gap to detect perturbations in a radial component of said primary magnetic flux caused by variations in properties of the material in the vicinity of said detector means; and means to shift circumferentially the location at which said detector means is operative in order that the position in the material of any detected variation in the properties thereof is ascertainable from the location at which said detection means is operative at the time and the position of the primary coils along the length of said material.

5. Apparatus as claimed in claim 4, in which said detector means comprises a ring of detectors disposed in said annular gap, and switching means is provided to connect said detectors sequentially to a signal processing circuit.

6. Apparatus as claimed in claim 4, in which said detector means comprises a secondary coil or coils, the coil or each such coil being arranged in said annular gap with its axis radial to the axis of said primary coils.

* * * * *